United States Patent [19]

Salzburg et al.

[11] Patent Number: 4,506,086

[45] Date of Patent: Mar. 19, 1985

[54] PROCESS FOR THE PRODUCTION OF DIANHYDROHEXITOL MIXTURES AND LIQUID MIXTURE OF DIANHYDROHEXITOLS

[75] Inventors: Herbert Salzburg; Manfred Hajek, both of Cologne; Holger Meyborg, Odenthal, all of Fed. Rep. of Germany

[73] Assignee: Bayer Aktiengesellschaft, Leverkusen, Fed. Rep. of Germany

[21] Appl. No.: 515,411

[22] Filed: Jul. 20, 1983

[30] Foreign Application Priority Data

Aug. 6, 1982 [DE] Fed. Rep. of Germany ....... 3229412

[51] Int. Cl.$^3$ ............................................ C07D 493/04
[52] U.S. Cl. ..................................... 549/464; 528/56; 528/65
[58] Field of Search ........................................ 549/464

[56] References Cited

FOREIGN PATENT DOCUMENTS 3041626 5/1982 Fed. Rep. of Germany .
3041673 6/1982 Fed. Rep. of Germany .

OTHER PUBLICATIONS

Fletcher et al., J.A.C.S., vol. 68, (1946), pp. 939-941.
Fauconier, Bull. Soc. Chem., (1884), 41, 119.
L. F. Wiggins, J. Chem. Soc., 1945, 4.
Haworth, Heath, Wiggins, J. Chem. Soc., 1944, 155.
R. Montgomery, L. F. Wiggins, J. Chem. Soc., 1947, 433.
J. C. Goodwin, J. E. Hodge, D. Weisleder, Carbohydr. Res. 79, 133, (1980).
S. Soltzberg, Advances Carbohydr. Chem. 25, 229, (1970).
L. F. Wiggins, Adv. Carbohydrate Chem. 5, 191, (1950).
L. W. Wright et al., J. Org. Chem., 29, pp. 2979-2982, (1964).

*Primary Examiner*—Henry R. Jiles
*Assistant Examiner*—Bernard I. Dentz
*Attorney, Agent, or Firm*—Gene Harsh; Joseph C. Gil; Lyndanne M. Whalen

[57] ABSTRACT

Liquid dianhydrohexitol mixtures are prepared from diacylation products of hexitols and compounds such as organic carboxylic acids, carboxylic acid anhydrides, carboxylic acid halides, ketene and carbonic acid ester derivatives. More specifically, such diacylation products are simultaneously dehydrated and isomerized by subjecting them to a temperature of at least 130° C. in the presence of a strong acid to yield diacylated dianhydrohexitol isomer mixtures. These isomer mixtures are then converted to dianhydrohexitol isomer mixtures by hydrolysis or transesterification. Suitable strong acids include proton acids, Lewis acids and heterogeneous acid catalysts (e.g., ion exchange resins). The mixtures of the present invention are characterized by a minimal tendency towards crystallization. These mixtures are particularly useful as chain extending agents in the production of polyurethanes.

9 Claims, No Drawings

PROCESS FOR THE PRODUCTION OF DIANHYDROHEXITOL MIXTURES AND LIQUID MIXTURE OF DIANHYDROHEXITOLS

BACKGROUND OF THE INVENTION

This invention relates to a process for the production of 1,4-3,6-dianhydrohexitol isomer mixtures from hexitols. The present invention also relates to isomer mixtures produced by this process and the use of those isomer mixtures as chain-extending agents in the production of polyurethanes.

1,4-3,6-dianhydrohexitols have been known since about 1880. These compounds have been described, for example, in Fauconier, Bull Soc. Chem. (1884) 41, 119; L. F. Wiggins, J. Chem. Soc. 1945, 4; Haworth, Heath, Wiggins, J. Chem. Soc. 1944, 155; R. Montgomery, L. F. Wiggins, J. Chem. Soc. 1947, 433; J. C. Goodwin, J. E. Hodge, D. Weisleder, Carbohydr. Res. 79, 133 (1980); S. Soltzberg, Advances Carbohydr. Chem., 25, 229 (1970); Ropuszynski et al, Przem. Chem. 48, (11), 665–668 (1969); German Offenlegungsschriften No. 3,041,673 (EP-52295) and 3,041,626; and L. F. Wiggins, Adv. Carbohydrate Chem. 5, 191 (1950).

One feature common to all of the known syntheses is that they produce a dianhydrohexitol which corresponds to the hexitol starting material in yields which vary considerably. The main disadvantages of these syntheses include unsatisfactory yields, formation of resin-like reaction residues and, a commercially disadvantageous high crystallinity of the products. Due to the pronounced tendency towards crystallization of the dianhydrohexitols, isomer mixtures which remain liquid at room temperature and do not crystallize cannot be obtained simply by mixing various isomers. Accordingly, if the anhydrohexitols are to be used, in the production of polyurethanes, for example, there is a need to produce them in a solvent-free liquid form because liquids are easier and less complicated to handle during processing. Keeping the substance liquid by fusion, for example, represents an additional energy-consuming process which further complicates processing.

Little is known about the isomerization reactions of dianhydrohexitols from the literature. Only L. W. Wright et al, J. Org. Chem. 29, 2979 (1964) appears to have succeeded in isomerizing dianhydrohexitols by heat treatment at very high temperatures (222°–240° C.) in an autoclave in the presence of hydrogenation catalysts and hydrogen under high pressure (150 atmospheres). However, this disclosed isomerization reaction cannot be successfully carried out in the absence of hydrogen under high pressure.

Applicants' own experiments have shown that dianhydrosorbitol is a suitable unit for the isocyanate polyaddition process, as is dianhydromannitol. However, both substances are solids at room temperature and cannot be prevented from crystallizing, even in mixtures.

SUMMARY OF THE INVENTION

It is an object of the present invention to provide liquid 1,4-3,6-dianhydrohexitol isomer mixtures having a reduced tendency to crystallize.

It is also an object of the present invention to provide a process for the production of liquid 1,4-3,6-dianhydrohexitol isomer mixtures having a reduced tendency to crystallize.

It is a further object of the present invention to provide a process for the production of liquid dianhydrohexitols in which secondary products and monoanhydro-compounds are formed in very small quantities.

These and other objects which will be apparent to those skilled in the art are accomplished by eliminating water from a diacylation product of a hexitol and compound selected from the group consisting of organic carboxylic acids, carboxylic acid anhydrides, carboxylic acid halides, ketene and carbonic acid ester derivatives. This dehydration is carried out in the presence of a strong acid at a temperature of at least 130° C. The thus-formed diacylated dianhydrohexitol isomer mixture is then converted into a dianhydrohexitol isomer mixture, for example by hydrolysis or transesterification.

DETAILED DESCRIPTION OF THE INVENTION

It has now surprisingly been found in the process of the present invention isomerization occurs during the dehydration of hexitols to the (di)acylated hexitol stage, at elevated temperatures using acid catalysts. Generally, any proton and/or Lewis acid is a suitable acid catalyst. Dianhydrohexitol isomer mixtures are obtained after hydrolysis. For example, a mixture of 1,4-3,6-dianhydrosorbitol, 1,4-3,6-dianhydromannitol and 1,4-3,6-dianhydroiditol is obtained when sorbitol is hydrolyzed in accordance with the present invention. Further, secondary products are formed in very small quantities and the quantity of monanhydro-compounds formed is minimal.

The isomer mixtures obtained by the isomerization reaction of the present invention are, unexpectedly, liquid and show very little tendency towards crystallization. In contrast, mixtures made up of individual components such as dianhydrosorbitol and dianhydromannitol retain a pronounced tendency towards crystallization, even after fusion.

It is surprising that the process of the present invention yields liquid dianhydrohexitol mixtures which in addition to dianhydrosorbitol, also give dianhydromannitol (relatively expensive when produced on its own) and dianhydroiditol (otherwise extremely difficult to obtain) from an inexpensive material like sorbitol. The dianhydroiditol is present in the isomer mixtures in quantities of from 0.5 to 12 wt. % and preferably in quantities of from 2 to 9 wt. %.

In the process of the present invention 1,4-3,6-dianhydrohexitol isomer mixtures having very little tendency towards crystallization are produced by eliminating water from hexitols in the presence of strong acids (preferably in the absence of water and solvents). More specifically, acylation products, preferably essentially diacylation products, formed with organic carboxylic acids, carboxylic acid anhydrides and/or carboxylic acid halides, ketene and carbonic acid ester derivatives are reacted by dehydration and isomerization at elevated temperatures (i.e., temperatures of at least 130° C., preferably in the range from 130° to 240° C. and most preferably in the range from 175° to 210° C.) in the presence of soluble proton or Lewis acids acting as acid dehydration reagents or heterogeneous acid catalysts to form the acylated (preferably diacylated) dianhydrohexitol isomer mixtures. The isomer mixture thus-obtained may then be converted by hydrolysis (preferably alkaline hydrolysis) or transesterification into the dianhydrohexitol isomer mixture.

The present invention also relates to isomer mixtures of 1,4-3,6-dianhydrohexitols, preferably 1,4-3,6-dianhydrosorbitol and 1,4-3,6-dianhydromannitol containing from 0.5 to 12 wt. % of 1,4-3,6-dianhydroiditol obtainable by isomerization reactions from hexitols (preferably from sorbitol and/or mannitol and, most preferably, from sorbitol) by the process of the present invention.

The present invention also relates to the use of the dianhydrohexitol isomer mixtures obtained in accordance with the present invention as chain-extending agents, optionally in admixture with conventional chain-extending agents, in the production of polyurethanes, preferably polyurethane elastomers.

The acylating agents used in the process of the present invention are carboxylic acids or their derivatives such as anhydrides, halides, less preferably esters, including carbonic acid ester derivatives.

The carboxylic acids suitable to the present invention include monocarboxylic acids corresponding to the general formula R—COOH, in which R represents an aliphatic (saturated or unsaturated), an aromatic or araliphatic radical. Specific examples of such carboxylic acids are formic acid, acetic acid, propionic acid, butyric acid, valeric acid, hexanic acid, benzoic acid, phenyl acetic acid, chloroacetic acid, trifluoroacetic acid and p-chlorobenzoic acid. Although di- and polycarboxylic acids may be used, they are not preferred.

Suitable acid halides include the halides (preferably acid chlorides or acid bromides) of the above-mentioned carboxylic acids. Specific examples of appropriate halides are acetyl chloride, propionyl chloride, hexanoyl chloride, benzoyl chloride, phenyl acetyl chloride, chloroformic acid esters, oxalyl chloride and acetyl bromide.

Suitable acid anhydrides are symmetrical or asymmetrical carboxylic acid anhydrides (for example acetanhydride, propionic acid anhydride) including mixed anhydrides of, for example, acetic acid and propionic acid or chloroformic acid esters and carboxylic acids.

Preferred acylating agents are acetic acid, acetyl chloride, ketene and most preferred is acetanhydride.

The acylating agents are generally used in a quantity of approximately 2 equivalents of groups having an acylating effect under the reaction conditions for each mole of hexitol because it is essentially diacylhexitol which is to be formed. In practice, the amount of acylating agent may vary between about 1.5 and 2.5 equivalents of acylating group for each mole of hexitol but is preferably kept between 1.9 and 2.2 equivalents. Where an excess of an acylating agent is used, the acylation reaction may be terminated before further reaction beyond the diacyl stage. A quantity of less than two equivalents of acylating groups for each mole of hexitol is less disadvantageous than an excess because, in a triacyl hexitol for example, the elimination of water to form the dianhydro compound is complicated and only some of the acyl groups are split during the elimination of water. In practice, some acylating agent may be lost, depending on the reaction apparatus and procedure used. This loss should be taken into account when calculating the quantity of acylating agent to be used.

The preferred method for carrying out the acylation reaction is dependent upon the specific acylating agent. For example, when acetic acid is used, esterification at high temperatures in the presence of an acid catalyst, preferably with continuous removal of water by distillation and where an excess is used, termination of the reaction on reaching the diacyl stage is preferred.

Where acetyl chloride is used, the acylation reaction is accompanied by elimination of HCl and the required stoichiometry should be maintained. If acetanhydride is used, the esterification is preferably carried out at elevated temperatures with the required stoichiometry being substantially maintained. More specifically, if the reaction is carried out in the absence of a catalyst, it is preferred to use approximately 2 moles of acetanhydride. Where an acid catalyst is used and the acetic acid formed is also esterified, approximately 1 mole of acetanhydride should preferably be employed. When ketene is used, the required stoichiometry should be substantially maintained.

Although the diacylhexitol stage may be isolated, the dehydration/isomerization stage is generally carried out immediately after acylation by removing any excess acylating agent and any reaction products still present (e.g., $H_2O$, HCl or carboxylic acids).

To eliminate water from the diacyl hexitol, the acid catalyst is added, optionally continuously over a prolonged period, and the hexitol is heated to an elevated temperature of at least 130° C., preferably in the range from 170° to 240° C. and most preferably in the range from 175° to 210° C. The water which forms is simultaneously distilled off. The acid catalyst is used in a quantity of from about 0.001 to 10 mole percent and preferably in a quantity of from 0.1 to 5 mole percent.

Depending upon the size of the batch and the apparatus used, the mixture is heated until the elimination of water is complete (for example, for 1 to 2 hours at 180° to 195° C.).

In addition to mineral acids (such as hydrochloric acids or hydrogen chloride, sulfuric acid, phosophoric acid, etc), other catalysts suitable for the dehydration and isomerization reactions of the diacyl hexitols to form the diacyl dianhydrohexitol isomers are Lewis acids (such as boron trifluoride, antimony pentachloride, tin-(IV)-chloride), acid ion exchangers based for example on diphenylbenzene crosslinked polystyrene sulfonic acid cation exchanger resins, acid zeolites, acid cracking and hydrocracking catalysts.

The anhydrohexitols formed may be isolated, for example by high vacuum distillation, in the form of high-boiling oils; or they may be further reacted directly from the dehydration/isomerization reaction stage (i.e. the diacyl group is split off to form the dianhydrohexitol mixtures). The acyl groups are generally split off by hydrolysis using aqueous bases (for example aqueous alkali hydroxides) or by (catalytic) transesterification (for example in alcohols) using a catalytic quantity of an alcoholate.

The dianhydrohexitol isomer mixture formed is recovered by fractional distillation in vacuo (optionally after neutralization) or may be obtained by extracting the aqueous reaction mixture with, for example, acetic acid alkyl esters or diethyl ketone.

From a practical point of view, it is particularly advantageous to carry out the isomerization process of the present invention with sorbitol and/or mannitol, preferably sorbitol, as the starting hexitol.

The 1,4-3,6-dianhydrohexitol isomer mixtures obtained by the process of the present invention are valuable units for the diisocyanate-polyaddition process. These isomer mixtures are also suitable as starters for polyethers (for example by the addition of ethylene oxide and/or propylene oxide), as units for polyesters, as starting polyol for polycarbonates, as hardeners for epoxide resins and as intermediate products for pharmaceuticals. These liquid dianhydrohexitol mixtures are particularly suitable for use as chain-extending agents for polyurethane elastomers.

In accordance with the present invention, the new dianhydrohexitol isomer mixtures are particularly useful in processes for the production of homogeneous and cellular polyurethane plastics. Such polyurethanes are prepared by reacting an organic polyisocyanate with a compound containing at least two Zerewitinoff-active hydrogen atoms and having a molecular weight of from 400 to 10,000, a chain-extending agent, optionally other short-chain compounds containing at least two Zerewitinoff-active hydrogen atoms and having a molecular weight of from 32 to 399 and optionally catalysts, blowing agents and other additives known to those skilled in the art. The chain-extending agent used is predominantly a liquid isomer mixture of 1,4-3,6-dianhydrohexitols, preferably 1,4-3,6-dianhydro-D-sorbitol and/or 1,4-3,6-dianhydro-D-mannitol in addition to isomer mixtures containing 1,4-3,6-dianhydroiditol. These mixtures may optionally be used in admixture with low molecular weight compounds preferably polyols having a molecular weight in the range from 62 to 250 and, more preferably, 1,4-butane diol.

When used as chain-extending agents, the isomer mixtures of the present invention yield high-quality elastomers and foams. In admixture with 1,4-butane diol for example, the dianhydrohexitol isomer mixtures may be used as chain-extending agents in liquid, low-viscosity form without any tendency to crystallize out.

Suitable polyisocyanates (preferably diisocyanates) for the production of polyurethanes are described in German Offenlegungsschrift No. 2,920,501, page 13, line 13 to page 16. Preferred polyisocyanates are the commercially readily obtainable polyisocyanates such as 2,4- and 2,6-tolylene diisocyanate and mixtures of these isomers (TDI); polyphenyl-polymethylene polyisocyanates of the type obtained by condensing aniline with formaldehyde, followed by phosgenation (crude MDI); 4,4-diphenylmethane diisocyanate (MDI); 3,3'-dimethyl-4,4'-diisocyanatobiphenyl and 1,5-naphthylene diisocyanate. 1,5-naphthylene diisocyanate and 4,4'-diphenylmethane diisocyanate are particularly preferred.

In addition to compounds containing amino groups, thiol groups or carboxyl groups, preferred starting components containing at least two isocyanate-reactive hydrogen atoms and having a molecular weight of generally from 400 to 10,000 are compounds containing hydroxyl groups, particularly compounds containing from two to eight hydroxyl groups, especially those having molecular weights in the range from 400 to 10,000 and preferably in the range from 1000 to 6000. Specific examples of such materials are polyesters, polyacetones, polyethers, polythioethers, polyacetals, polycarbonates and polyester amides containing at least two, generally two to three hydroxy groups, of the type known to those skilled in the art to be useful in the production of homogeneous and cellular polyurethanes.

The polyesters containing hydroxyl groups suitable for use in accordance with the present invention include: the reaction products of polyhydric, preferably dihydric and, optionally, tri- and tetrahydric alcohols with polybasic, preferably dibasic carboxylic acids. The polycarboxylic acids may be aliphatic, cycloaliphatic, aromatic and/or heterocyclic in nature and may optionally be substituted, for example, by halogen atoms and/or unsaturated. Examples of such polycarboxylic acids and derivatives thereof are adipic acid, sebacic acid, phthalic acid, phthalic acid anhydride, tetrahydro- or hexahydrophthalic acid anhydride, isophthalic acid, trimellitic acid, maleic acid anhydride, di- and trimerized unsaturated fatty acids, terephthalic acid dimethyl ester and terephthalic acid-bis-2-hydroxyethyl ester.

Suitable polyhydric alcohols include: ethylene glycol; propylene glycol; 1,4- and/or 2,3-butane diol; 1,6-hexane diol; neopentyl glycol; 1,4-bis-hydroxymethyl cyclohexane; hydroquinone-bis-(hydroxyethylether); 2-methyl-1,3-propane diol; glycerol; trimethylol propane; 1,2,6-hexane triol; pentaerythritol; quinitol, mannitol, sorbitol; formitol; methyl glycoside; also di-, tri-, tetra- and higher polyethylene, polypropylene and polybutylene glycols.

The polyesters may contain terminal carboxyl groups. Polyesters of lactones, for example ε-caprolactone, or hydroxy carboxylic acids, for example, ε-hydroxycaproic acid, may also be used.

The polyethers containing at least 2, generally 2 to 8 and preferably 2 to 3 hydroxyl groups which may be used in accordance with the present invention are also known to those in the art. These polyethers may be obtained for example by polymerization of tetrahydrofuran and/or epoxides, such as ethylene oxide, propylene oxide, butylene oxide, styrene oxide or epichlorohydrin, themselves (optionally in the presence of Lewis catalysts), or by the addition of these epoxides (preferably ethylene oxide and propylene oxide) optionally in admixture or successively, with starter components containing reactive hydrogen atoms. Appropriate starter components include: water and ammonia; alcohols such as ethylene glycol, propylene glycol, diethylene glycol, dimethylol propane, glycerol, sorbitol, sucrose, formitol, formose and 4,4'-dihydroxydiphenyl propane; and amines such as aniline, ethylene diamine and ethanolamine. OH-group containing polythioethers, polybutadienes, polyacetals, polycarbonates or polyester amides are also suitable starting products.

Representatives of the above-mentioned, relatively high molecular weight polyhydroxyl compounds suitable for use in accordance with the present invention are described, for example, in High Polymers, Vol. XVI, "Polyurethanes, Chemistry and Technology" by Saunders-Frisch, Interscience Publishers, New York/London, Vol. I, 1962, pages 32 to 42 and pages 44 to 54, and Vol. II, 1964, pages 5 to 6 and 198 to 199; in Kunststoff-Handbuch, Vol. VII, Vieweg-Hochtlen, Carl-Hanser-Verlag, Munich, 1966, for example on pages 45 to 71; and German Offenlegungsschrift No. 2,920,501, pages 17 to 24. It is of course possible to use mixtures of the above-mentioned compounds, for example mixtures of polyethers and polyesters.

In accordance with the present invention, the liquid isomer mixtures from the series of 1,4-3,6-dianhydrohexitols useful as chain extending agents correspond to the general formula:

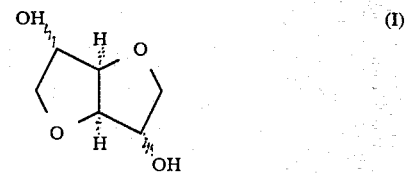

(I)

It is preferred to use mixtures containing predominant quantities of 1,4-3,6-dianhydro-D-sorbitol (formula II) and 1,4-3,6-dianhydro-D-mannitol (formula III) in addition to dianhydroiditol (IV).

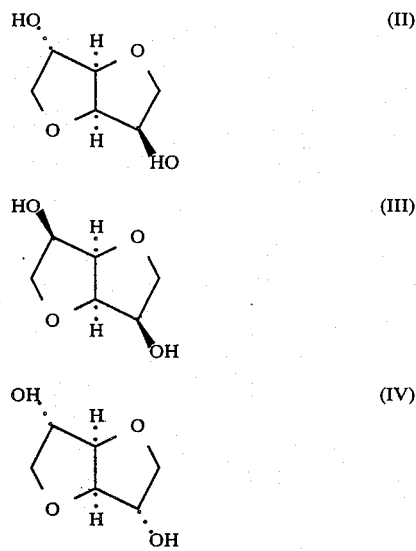

The chain extender isomer mixtures according to the invention may also be used in the form of other mixtures with other 1,4-3,6-dianhydrohexitols.

Mixtures of the bis-anhydrohexitol isomers of the present invention with other short-chained compounds having a molecular weight in the range from 32 to 399 (preferably diols having a molecular weight in the range from 62 to 250) may also be used as a chain extending agent in the production of polyurethanes. Examples of such short-chained compounds containing hydroxyl groups and/or amino groups and/or thiol groups and/or carboxyl groups (preferably hydroxyl groups and//or amino groups) are low molecular weight polyols and/or amino alcohols having a molecular weight in the range from 62 to 399, such as ethylene glycol; 1,2- and 1,3-propane diol; 1,4-butane diol; 2,3-butane diol; 1,5-pentane diol; 1,6-hexane diol; 1,8-octane diol; neopentyl glycol; 1,4-bis-hydroxymethyl cyclohexane; 2-methyl-1,3-propane diol; trimethylol propane; 1,2,6-hexane triol; trimethylol ethane; pentaerythritol; quinitol; mannitol; sorbitol; castor oil; di- and tetraethylene diol; higher polyethylene glycols; di- tri- and higher polypropylene diols; di- tri- and higher polybutylene diols having a molecular weight of up to 399 (preferably up to 250); 4,4'-dihydroxy diphenyl propane; dihydroxy ethyl hydroquinone; terephthalic acid bis-(2-hydroxyethyl)-ester; ethanolamine; diethanolamine and N-methyl diethanolamine.

Examples of appropriate aromatic diamines are bis-anthranilic acid esters (German Offenlegungsschriften Nos. 2,040,644 and 2,160,590); 3,5- and 2,4-diaminobenzoic acid esters (German Offenlegungsschrift No. 2,025,900); diamines containing ester groups; diamines containing ether groups; 2-halogen-1,3-phenylene diamines optionally substituted in the 5-position; 3,3'-dichloro-4,4'-diaminodiphenyl methane; tolylene diamines; 4,4'-diaminodiphenyl methane; 4,4'-diaminodiphenyl sulfide; diaminodiphenyl dithioether; aromatic diamines substituted by alkylthio groups; diaminobenzene phosphonic acid esters; aromatic diamines containing sulfonate or carboxylate groups and the high-melting diamines disclosed in German Offenlegungsschrift No. 2,635,400. Examples of aliphatic-aromatic diamines are the aminoalkyl thioanilines.

Examples of surface-active additives, foam stabilizers, cell regulators, reaction retarders, stabilizers, flameproofing agents, plasticizers, dyes, fillers, fungicides and bactericides which may optionally be used to produce polyurethanes in accordance with the present invention and information on the way in which they are used can be found in Kunststoff-Handbuch, Vol. VII, by Vieweg and Hochtlen, Carl-Hanser-Verlag, Munich 1966, for example on pages 103 to 113, and in German Offenlegungsschrift No. 2,920,501.

In accordance with the present invention, the reaction components may be reacted by the known one-shot process or by the prepolymer process. Information on processing machines which may be used to carry out such reactions can be found in Kunststoff-Handbuch, Vol. VII, by Vieweg and Hochtlen, Carl-Hanser-Verlag, Munich, 1966, for example on pages 121 to 247.

In the process of the present invention, the quantity of reaction components used is generally such that the molar ratio of polyisocyanates to chain extender plus compounds containing reactive OH-groups is between 0.9 and 1.3, preferably to between 0.95 and 1.25. The optimum ratio will depend upon the particular processing technique used. If a prepolymer process is used, the percentage NCO-content of the prepolymer may be between 1 and 18 wt. % (preferably between 3 and 16 wt. %). The molar ratio of reactive hydrogen in the chain extender to relatively high molecular weight polyhydroxyl compounds may vary within wide limits but is preferably between 0.5 and 15. Flexible to rigid polyurethanes may be obtained.

In another embodiment of the present invention, the relatively high molecular weight compound containing at least 2 hydroxyl groups is reacted in admixture with the chain extending agent in an excess of diisocyanate. After granulation, the reaction product is formed under heat and pressure. Polyurethane plastics varying both in their rigidity and in their flexibility may be obtained (depending upon the molar ratios in which the reactants are used). It is also possible to produce plastics which may be processed in the same way as thermoplastics. In another embodiment of the present invention, the relatively high molecular weight compound containing at least two hydroxyl groups is reacted in admixture with the chain-extending agent and a substoichiometric quantity of diisocyanate, resulting in the formation of a rollable sheet which may subsequently be converted (e.g. by crosslinking with more diisocyanate) into a rubber-elastic polyurethane plastic.

The dianhydrohexitol mixtures produced in accordance with the present invention or mixtures thereof with diols are particularly suitable for use in the elastomer casting process with NCO-prepolymers (based on substantially linear polyesters, polylactones and/or polycarbonates—molecular weights 1000 to 4000) and excess quantities of naphthylene-1,5-diisocyanate having an NCO-content of from 3 to 16%.

Elastomers produced in accordance with the present invention may be used for a variety of applications such as moldings subject to severe mechanical stressing, rollers, V-belts or seals subjected to severe thermal or chemical stressing, hot-water pipes, motors and in the production of films, textile coatings and polyurethane powders. In addition to homogeneous elastomers, it is also possible to produce cellular polyurethanes (flexible to rigid foams).

The process of the present invention is illustrated by the following Examples in which the figures given represent parts or percentages by weight.

EXAMPLES

EXAMPLE 1

2 g of concentrated sulfuric acid were added to 1 mole of sorbitol (182 g) and 170 g of acetic acid. This mixture was heated to an internal temperature of approximately 105° C. and water was distilled off through a column. After the water had been distilled off, the reaction mixture was neutralized by addition of semi-concentrated sodium hydroxide distilling the excess of acetic acid and water in vacuo. After three distillations with toluene (3 times with 200 ml of toluene) the water and acetic acid were completely removed and the statistically acylated diacetate recovered.

EXAMPLE 2

1 mole of sorbitol (182 g) and 2 moles of acetic acid anhydride (204 g) were heated together to an internal temperature of approximately 120° to 130° C., and then refluxed for 2 hours using a highly effective reflux condenser until the reflux temperature had reached 118° C. The acetic acid was distilled off in the same way as described in Example 1.

EXAMPLE 3

2 moles of acetyl chloride were added at room temperature to 1 mole of sorbitol (182 g) and heated. Hydrogen chloride was given off. Initially, acetyl chloride boiled off under reflux. Thereafter, the internal temperature was increased to approximately 100° C.

Neutralization was carried out with sodium acetate and the reaction mixture was worked up in the same way as in Example 1. The residual sodium chloride did not interfere with further processing.

Where sorbitol or mannitol in the form of an aqueous solution was reacted by the procedures used in Examples 1 to 3, the water from the solution had to be distilled off before carrying out the isomerization reaction.

EXAMPLE 4

2 moles of hexitol diacetate and 3 g of concentrated sulfuric acid were heated over a period of from about 1 to 1.25 hours to a heating bath temperature of 180° to 190° C. Water was distilled off. After 1.25 hours, a 30% aqueous solution containing 2.2 g of sodium hydroxide was carefully added dropwise to the reaction mixture, followed by fractionation. A pale yellow oil of the dianhydrohexitol diacetate distilled over at 170°-200° C./26 mbar. Virtually no residue remained except for the salt.

Instead of sulfuric acid, p-toluene sulfonic acid, hydrogen chloride, boron trifluoride etherate, etc. could also have been used.

EXAMPLE 5

The distillate of Example 4 was dissolved in ethanol to form a 60% solution which was then adjusted to pH 9-10 with sodium methylate. After 5 hours at room temperature, the mixture was neutralized with dilute hydrochloric acid and distilled. 232 g of pale yellow dianhydrohexitol mixture (approximately 80% of theoretical) based on 2 moles of sorbitol according to Examples 1-3 were obtained. Analysis by gas chromatography showed the mixture contained about 7 to 12% of dianhydromannitol, 79 to 83% of dianhydrosorbitol, 6 to 9% of dianhydroiditol and up to about 4% of mono- di- and trihydroxyfunctional impurities.

Hydrolysis with aqueous sodium hydroxide or with other standard bases produced substantially the same result.

The process may of course be carried out without isolating the intermediate mixture. This is illustrated by the following Example.

EXAMPLE 6

730 g of a 50% aqueous solution of 70 parts of sorbitol and 30 parts of mannitol were concentrated in vacuo (20 mm) at 100° C. to form an oil to which, after the distillation of water had stopped, 180 g of acetanhydride and 6.5 g of p-toluene sulfonic acid $H_2O$ were added. After heating to 130°-140° C., water and acetic acid were again distilled off. The temperature was then raised to 180°-190° C. (heating bath temperature) over a period of 1 to 1.5 hours during this ring-closing reaction, water was distilled off.

When the water had been completely removed, the reaction mixture was cooled to around 100°-130° C. and a solution of 3.76 g of sodium methylate in 40 ml of n-butanol was added dropwise. The basic mixture was kept at 130° C. for about 20 minutes, after which another 6.5 g of p-toluene sulfonic acid $H_2O$ were added to neutralize the solution. Fractionation in vacuo gave 232 g of pale yellow dianhydrohexitol mixture (80% of the theoretical).

According to gas chromatographic analysis the mixture contained 29 to 33% dianhydromannitol, 57 to 62% dianhydrosorbitol, 6 to 9% dianhydroiditol and up to about 4% of mono- di- and trihydroxyfunctional impurities.

EXAMPLE 7

2 moles of sorbitol (364 g) were melted at 130° to 140° C. and 2 moles of acetic anhydride (204 g) added dropwise to the resulting melt. The acetic acid which formed during the acylation reaction boiled under reflux. After about 15 minutes, 3 g of concentrated sulfuric acid were added. While the temperature of the heating bath was increased over a period of 1 to 1.5 hours to 180°-190° C., water was spontaneously formed and distilled off. After 1.5 hours, a 30% aqueous solution containing 2.2 g of NaOH was carefully added dropwise to neutralize the mixture which was then subjected to fractional distillation. A pale yellow oil of the diacetyl-dianhydrohexitol mixture distilled over at 170° to 200° C./26 mbar with hardly any residue remaining other than salt.

Sodium methylate was added to the oil in 300 ml of methanol until the pH reached 10, and this mixture was refluxed. On completion of deacetylation, the mixture was neutralized with sulfuric acid and subjected to fractional distillation. First runnings of ethyl acetate and alcohol were obtained, after which the pale yellow product of the dianhydrohexitol isomer mixture (an oil) distilled over at 170°-190° C./26 mbar. Yield: 252 g=86% of the theoretical.

The oil is dianhydrosorbitol, dianhydromannitol and dianhydroiditol remained liquid for months.

EXAMPLE 8

250 parts of a polyester produced from adipic acid and ethylene glycol and having an average molecular weight of 2000 were dehydrated at 120° C. in a vacuum of 14 mbar. 44.6 parts of 1,5-naphthalene diisocyanate were then added and the temperature kept at 130° C. for 30 minutes to form an NCO-prepolymer. Equivalent (OH/NCO=1:1) quantities of the liquid isomer mixture produced in Example 7 and 0.035 part of tin(II)-octoate were then added to the prepolymer with vigorous stirring at 110° C. After stirring for 30 seconds, the mixture was poured into a mold preheated to 110° C. The mixture was pourable for 3 to 4 minutes. After tempering for 24 hours at 110° C., the homogeneous elastomer obtained had the following properties:

| | |
|---|---|
| Tensile strength: | 32.3 MPa |
| Breaking elongation: | 650% |
| Structural strength: | 500 N |
| Shore A hardness: | 75 |
| Elasticity: | 41% |

EXAMPLE 9

200 parts of a mixed polyester of adipic acid, ethylene glycol and 1,4-butane diol (1:1) (molecular weight 2000), were dehydrated for 30 minutes at 13 mbar/130° C., 80 parts of 1,5-naphthalene diisocyanate were added to this dehydrated mixture. After 30 minutes at 130° C., the mixture thus-produced was cooled to 110° C. A mixture of 34 parts of the dianhydrohexitols produced in Example 7 and 0.067 parts of triethylene diamine (DABCO ®) were then stirred into the mixture and the mixture was cast after 30 seconds. The mixture remained pourable for 2 minutes. After tempering for 24 hours at 110° C., the product had the following properties:

| | |
|---|---|
| Tensile strength: | 22.8 MPa |
| Breaking elongation: | 310% |
| Structural strength: | 630 N |
| Shore A hardness: | 96 |
| Elasticity: | 39%. |

EXAMPLE 10

A liquid, non-crystallizing mixture was prepared from 91.7 parts of 1,4-3,6-dianhydro-D-hexitols corresponding to those produced in Example 7 and 9.1 parts of 1,4-butane diol. 0.66 part of DABCO ® (sold by Air Products) were added to 32.2 parts of the mixture thus-prepared. The resulting mixture was then stirred with the prepolymer of Example 9. This mixture remained pourable for 6 minutes. The elastomer obtained had the following properties:

| | |
|---|---|
| Tensile strength: | 22.5 MPa. |
| Breaking elongation: | 310% |
| Structural strength: | 590 N |
| Shore A hardness: | 93 |
| Elasticity: | 37% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of liquid 1,4-3,6-dianhydrohexitol isomer mixtures having a minimal tendency to crystallize comprising:
   (a) dehydrating and isomerizing a diacylation product of (i) a hexitol and (ii) a compound selected from the group consisting of organic carboxylic acids, carboxylic acid anhydrides, carboxylic acid halides, ketene, carbonic acid ester derivatives and mixtures thereof at a temperature of at least 130° C. in the presence of a strong acid to form a diacylated dianhydro-hexitol isomer mixture; and
   (b) converting the isomer mixture produced in (a) into a dianhydrohexitol isomer mixture.

2. The process of claim 1 in which step (b) comprises hydrolyzing the isomer mixture produced in step (a).

3. The process of claim 1 in which step (b) comprises transesterifying the isomer mixture produced in step (a).

4. The process of claim 1 in which the compound (ii) is selected from the group consisting of acetic acid, acetic anhydride and acetyl chloride.

5. The process of claim 1 in which the strong acid employed in step (a) is selected from the group consisting of proton acids, Lewis acids, heterogeneous acid catalysts and mixtures thereof.

6. The process of claim 1 in which step (a) is carried out at a temperature in the range of from 175° to 210° C.

7. The process of claim 1 in which the hexitol (i) is sorbitol or mannitol.

8. The process of claim 1 in which the hexitol (i) is a 95:5 to 5:95 mixture of sorbitol and mannitol.

9. A liquid isomer mixture of 1,4-3,6-dianhydrosorbitol and 1,4-3,6-dianhydromannitol containing from 2 to 9 wt. % 1,4-3,6-dianhydroiditol.

* * * * *